(12) United States Patent
Mao et al.

(10) Patent No.: US 8,169,680 B2
(45) Date of Patent: May 1, 2012

(54) POLYMERS RESPONSIVE TO RADIATION PRESSURES

(75) Inventors: Hanbin Mao, Kent, OH (US); Paul Luchette, Kent, OH (US); David E. Bergbreiter, College Station, TX (US)

(73) Assignees: Kent State University, Kent, OH (US); The Texas A&M University System, College Station, TX (US)

( * ) Notice: Subject to any disclaimer, the term of this patent is extended or adjusted under 35 U.S.C. 154(b) by 738 days.

(21) Appl. No.: 11/901,916

(22) Filed: Sep. 19, 2007

(65) Prior Publication Data

US 2009/0296187 A1   Dec. 3, 2009

Related U.S. Application Data

(60) Provisional application No. 60/846,027, filed on Sep. 20, 2006.

(51) Int. Cl.
| | |
|---|---|
| *G02F 1/03* | (2006.01) |
| *G02F 1/07* | (2006.01) |
| *F21V 9/00* | (2006.01) |
| *G02B 5/02* | (2006.01) |
| *G02C 7/10* | (2006.01) |
| *G02F 1/361* | (2006.01) |
| *G03B 11/00* | (2006.01) |

(52) U.S. Cl. ........ 359/241; 359/288; 359/321; 359/885; 359/886; 252/582

(58) Field of Classification Search .................. 252/582; 359/241, 321, 288, 358–359, 885, 886; 442/394, 442/399, 59, 118, 164, 374; 428/364, 394, 428/395; 604/358, 365, 366, 367, 372, 373, 604/385.18, 385.201, 385.23, 304, 904

See application file for complete search history.

(56) References Cited

U.S. PATENT DOCUMENTS

| | | | | |
|---|---|---|---|---|
| 5,095,515 | A | * | 3/1992 | Seaver ............................ 385/16 |
| 5,368,781 | A | | 11/1994 | Haacke et al. |
| 6,014,246 | A | * | 1/2000 | Asher et al. .................... 359/288 |
| 6,097,530 | A | | 8/2000 | Asher et al. |
| 6,165,389 | A | | 12/2000 | Asher et al. |
| 6,451,429 | B2 | * | 9/2002 | Mumick et al. ............... 428/394 |

OTHER PUBLICATIONS

Hanbin Mao, Chunmei Li, Yanjie Zhang, Steven Furyk, Paul S. Cremer, and David E. Bergbreiter, High-Throughput Studies of the Effects of Polymer Structure and Solution Components on the Phase Separation of Thermoresponsive Polymers, Macromolecules 2004, 37, 1031-1036.2004 American Chemical Society.*

* cited by examiner

*Primary Examiner* — Mark Kopec
*Assistant Examiner* — Bijan Ahvazi
(74) *Attorney, Agent, or Firm* — Hudak, Shunk & Farine Co. LPA

(57) ABSTRACT

Polymers that undergo a reversible phase change in response to being exposed to a light from a laser having a radiation pressure greater than a threshold level. The phase changeable polymers have the ability to reduce the intensity of the laser and can advantageously scatter laser light incident on the polymers. The on-off response of such polymers is in the microsecond range and the light scattering property is independent of laser wavelength. The polymers can beneficially be incorporated into devices to protect human vision and optical instruments that are vulnerable to lasers at high intensities. Methods for making and using such devices are also disclosed.

13 Claims, 2 Drawing Sheets

POLYMERS RESPONSIVE TO RADIATION PRESSURES

CROSS REFERENCE

This application claims the benefit of priority under 35 U.S.C. §119 of U.S. Provisional Application Ser. No. 60/846,027 filed on Sep. 20, 2006.

FIELD OF THE INVENTION

The present invention relates to polymers that undergo a reversible phase change in response to being exposed to light or radiation, such as from a laser having a radiation pressure greater than a threshold level. The phase changeable polymers have the ability to reduce the intensity of the incident light or radiation and can advantageously scatter the same. The on-off response time of such polymers is in the microsecond range and the scattering property is independent of light or radiation wavelength. The polymers can beneficially be incorporated into devices to protect human vision and optical instruments that are vulnerable to light or radiation at high intensities or pressures. Methods for making and using such devices and compositions including the polymers are also disclosed.

BACKGROUND OF THE INVENTION

Poly(N-isopropylacrylamide) (PNIPAM) is well known to be sensitive to temperature, chemical species and concentrations. At low temperatures for example, the polymer has an extended chain configuration and is soluble in aqueous solvent. Above the lower critical solution temperature (LCST~32° C.), the polymer folds and precipitates from solution. The process is driven by increased entropy in the system. Below LCST, water molecules align along the extended chain of the polymer. As PNIPAM becomes folded when the temperature is above LCST, these organized water molecules are lost to the bulk with less ordered structures, increasing the total entropy of the system. The chemical species in various solutions can interfere with the interaction between water and polymer molecules and influence the PNIPAM phase transition. This property has made PNIPAM based materials desirable in the field of surface chemistry, catalysis, and biotechnology. In surface chemistry, for instance, PNIPAM has been used to construct a "smart" surface whose hydro-phobicity varies with temperature. This endows the self-cleaning property of a surface that repels aqueous contaminants above phase transition temperatures. Due to the simple structure, facile synthesis and easily accessible transition temperature (32° C.) of PNIPAM, the clouding process has become a model system to study protein cold denaturation, which shares a similar phase transition mechanism. Such broad applicability of PNIPAM implies profound impacts on many fields once a new property associated with the polymer is discovered. Crosslinked PNIPAM in a form of sol gel has been found to respond to radiation pressure.

U.S. Pat. No. 5,095,515 relates to an optical switch which comprises a photoelastic, optically transparent material whose index of refraction is changed by stress and which propagates an optical beam or beams from an inlet window to an outlet window in the material, with the inlet window adapted to receive an optical beam from an optical source and the outlet window adapted to pass an optical beam from the photoelastic material to an optical output receptor, and a receptor means of applying a stress gradient to said photoelastic material to change the index of refraction and hence, the optical path of the optical beam between a normal, unstressed optical beam path and a bent, stressed optical beam path. Optical systems are described in which the optical switch is reportedly employed to form optical lenses wherein an optical beam is focused by stress within an optical material, such as a photoelastic cylindrical rod. Optical integrated systems are also described employing the optical switch with optical devices as an optical integrated module.

U.S. Pat. No. 5,368,781 relates to a reportedly tunable, radiation filter comprising a highly ordered crystalline array of microparticles fixed in a polymerized hydrogel.

U.S. Pat. No. 6,014,246 relates to devices that comprise, mesoscopically periodic materials that combine crystalline colloidal array (CCA) self-assembly with the temperature induced volume phase transitions of various materials, preferably poly(N-isopropylacrylamide) (PNIPAM). In one embodiment, a PNIPAM CCA is formed in an aqueous media and contained within cell means. In another embodiment, a CCA of charged particles is formed and polymerized in a PNIPAM hydrogel. Methods for making these devices are also disclosed. The devices of the present invention are reportedly useful in many applications including, for example, optical switches, optical limiters, optical filters, display devices and processing elements. The devices are further reportedly useful as membrane filters. All of these devices reportedly have the feature of being tunable in response to temperature. Devices that reportedly change diffracted wavelength in response to mechanical pressure are also disclosed.

U.S. Pat. Nos. 6,097,530 and 6,165,389 relate to devices that comprise, mesoscopically periodic materials that reportedly combine crystalline colloidal array (CCA) self-assembly with the temperature induced volume phase transitions of various materials, preferably poly(N-isopropylacrylamide) (PNIPAM). In one embodiment, a PNIPAM CCA is formed in an aqueous media and contained within cell means. In another embodiment, a CCA of charged particles is formed and polymerized in a PNIPAM hydrogel. Methods for making these devices are also disclosed. The devices are reportedly useful in many applications including, for example, optical switches, optical limiters, optical filters, display devices and processing elements. The devices are further reportedly useful as membrane filters. All of these devices reportedly have the feature of being tunable in response to temperature. Devices that change diffracted wavelength in response to mechanical pressure are also disclosed.

There is a widespread application of lasers in daily life and in the military, such as on the battlefield. People routinely use lasers for scientific or business presentations, alignment in constructions and various entertaining purposes. On the battlefield, lasers have already been deployed to detonate explosive devices and destroy reconnaissance instruments containing optical components. Human vision can be irreversibly damaged by lasers, especially at infrared wavelengths to which eyes are not sensitive and, therefore, "blinking protection" is absent. Recent incidents include a Delta pilot who was hit in the eye by a laser beam while flying a 737 and a 20 year-old intern at Los Alamos National Lab who was blinded by a laser beam. It is imperative to construct devices to protect human vision and optical instruments that are vulnerable to laser light or radiation at high intensities. Some devices available today adopt passive mechanisms where there exists little discrimination against laser intensities across the device aperture that admits the light. As a result, imaging field is narrower and the sensitivity to the light at normal intensities suffers. Although optical limiters can respond to a laser beam according to its intensity, the spectrum in wavelength is limited.

In view of the above, it would be desirable to provide protective compositions, and to construct a device including such compositions to protect vision and optical instruments that are vulnerable to lasers at relatively high radiation pressure.

SUMMARY OF THE INVENTION

The present invention relates to polymers or copolymers, i.e. (co)polymers having the ability to reversibly change phases and/or properties when subjected to light, i.e., electromagnetic radiation, greater than a threshold radiation pressure. The phase changeable (co)polymer prior to exposure is substantially soluble in a solution and comprised preferably of substantially linear chains or crosslinked chains of relatively high molecular weight. Upon exposure to a sufficient radiation pressure, the (co)polymer folds, collapses, shrinks, or the like, thereby precipitating out of solution and aggregating, thereby attenuating and reducing the intensity of the light by scattering. The (co)polymer returns to a soluble state when the radiation pressure is reduced before the threshold level, substantially immediately. The precipitation and solubilizing responses can occur within microseconds.

The compositions of the present invention, including a phase changeable (co)polymer dispersed or suspended in a solution, can be incorporated into many devices, preferably optical devices, such as optical switches, optical limiters, optical filters, optical coatings and the like. Accordingly, the optical devices of the invention are useful in many applications including, but not limited to, light shutters, sensor protection in scientific, industrial, and medical instrumentation, eye protection and display devices. The devices are also useful for many military applications. Overall, the devices can be used with any product in which the disclosed radiation filtering characteristics are desirable.

Although it will be appreciated that any materials having the above-described characteristics can be used, it is preferred that the (co)polymer is poly(N-substituted)(meth)acrylamide polymer or copolymer, such as poly(N-isopropyl acrylamide) (PNIPAM) or a copolymer thereof, as PNIPAM exhibits a desirable radiation pressure induced phase transition. Accordingly, the optical devices of the present invention are capable of being switchable or tunable in response to radiation pressure changes.

It is an object of the present invention to provide a composition and further, an optical switching device comprising the composition which can operate to scatter certain wavelength bands of incident light.

It is a further object of the present invention to provide a composition and an optical switching device comprising the composition that scatters light in response to changes in radiation pressure of the light.

It is yet another object of the present invention to provide a composition and an optical device that functions as an optical limiter for potentially harmful radiation.

It is another object of the present invention to provide a composition and an optical device comprising the composition that operates to scatter certain wavelengths of radiation above a threshold pressure in a short period of time, such as microseconds.

One aspect of the invention is a radiation pressure activatable light filtering device, comprising a container having a substantially optically clear portion through which light can pass; and a composition disposed in the container comprising a linear or crosslinked poly(N-substituted)(meth)acrylamide (co)polymer having a weight average molecular weight greater than $2.1 \times 10^7$ g/mol in a solution, wherein the composition is substantially optically clear below a lower critical solution temperature of the composition, wherein the (co)polymer is capable of undergoing a reversible phase transition that forms microdomains having a different refractive index in the solution in response to being exposed to light having a radiation pressure above a threshold value thereby causing the light above the threshold value incident on the phase transformed (co)polymer to scatter, and wherein the (co)polymer is soluble in the solution below the lower critical solution temperature and prior to exposure to said light and soluble when exposed to light below the threshold intensity.

Another aspect of the invention is a method for scattering light utilizing a radiation pressure responsive device, comprising the steps of providing a radiation pressure responsive device, comprising a container having a substantially optically clear portion through which light can pass, said container comprising a composition comprising a linear or crosslinked poly(N-substituted)(meth)acrylamide (co)polymer to the container; and a solution, wherein the composition comprising the copolymer and the solution is substantially optically clear below a lower critical solution temperature of the composition, and wherein the copolymer is soluble in the solution below the critical solution temperature and prior to exposure to said light above a threshold value; and exposing said composition to light having a radiation pressure above the threshold value thereby causing the light above the threshold value incident on the phase transformed copolymer of the composition to scatter.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
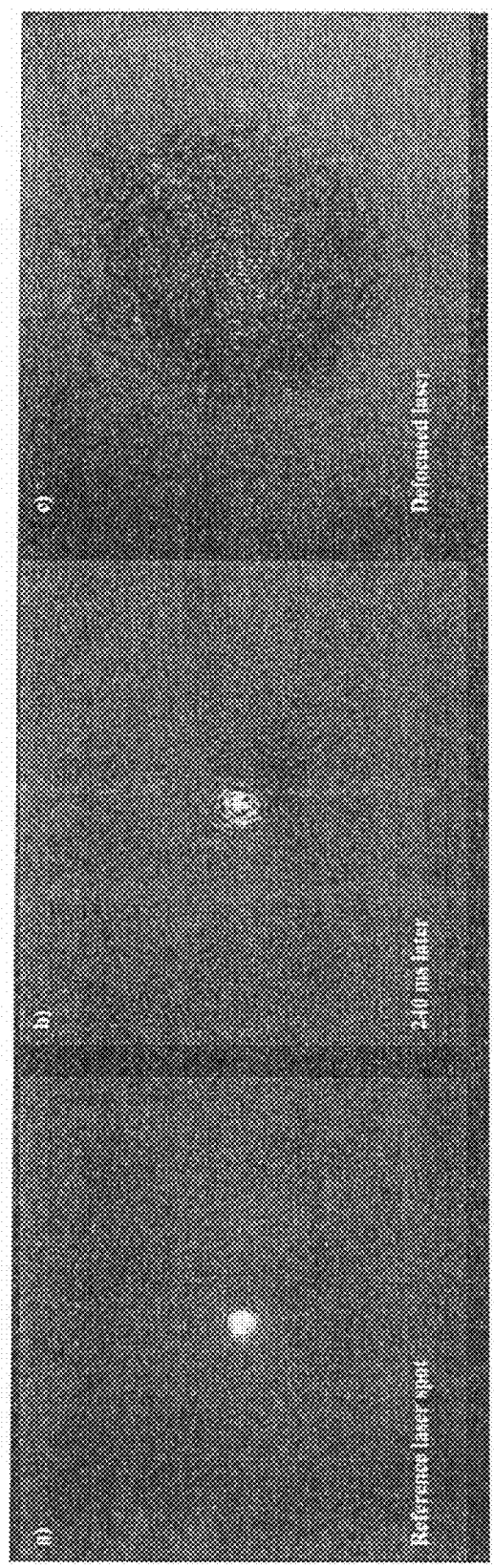
FIG. 1A is a photograph from a CCD camera of a reference laser spot formed immediately after passing light from a laser through a container including a composition comprising linear PNIPAM having $3.95 \times 10^7$ g/mol weight average molecular weight at a concentration of 10 mg/mL in deuterium at room temperature, wherein the light was emitted from a 1064 nanometer laser having a power of 224 mW.
FIG. 1B is a photograph showing a laser spot on the substrate 240 ms after the 224 mW 1064 nm laser was aimed through the container wherein scattering of the light particles has appeared at the laser focus and surrounding area whereby the radiation pressure of the laser light was reduced.
FIG. 1C is a photograph showing that the light passing through the container and composition was defocused, showing much increased light scattering and much reduced laser intensity or radiation pressure.

The compositions of the present invention comprise a phase changeable polymer or copolymer, hereinafter (co) polymer, in a carrier such as a solution in which the (co) polymer is substantially soluble, wherein the polymer is preferably dispersed in the appropriate carrier and is able to undergo a phase transition in response to changes in radiation pressure. The composition can be utilized in substantially any optical device where desired.

The phase changeable (co)polymer is a material that is sensitive to radiation pressure, such as from a laser beam of a laser generally having an intensity that is Gaussian or having a standard distribution, and precipitates, from a composition at a temperature below a lower critical solution temperature prior to exposure to the radiation pressure, in response to relatively high radiation pressure and thereby reduces laser intensity by scattering. The precipitated polymer particles resolublize when the triggering force, i.e., light above a threshold radiation pressure is removed.

In a preferred embodiment, the phase changeable (co)polymer is a (meth)acrylamide polymer or copolymer wherein the nitrogen atom has a pendant group connected thereto, such as an aliphatic group, an aromatic group, a cyclic group, or a combination thereof, or a group that forms a ring including the nitrogen atom, of one or more, preferably two or more carbon atoms and optionally one or more heteroatoms. The term "(meth)" means that the methylene group is present or absent. The poly(N-substituted)(meth)acrylamide polymer or copolymer thus contains a repeat unit comprising the following formula:

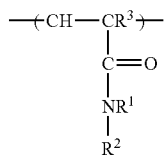

wherein each $R^1$ and $R^2$, independently, is hydrogen, a linear or branched aliphatic group such as an alkyl group, an aromatic group, an aryl-aliphatic group, cyclic group, a heterocyclic group including the nitrogen atom, or one of the above groups chemically modified with a non-carbon atom or other chemical groups such, as a functional group, which includes but is not limited to fluoride; wherein the $R^1$ or $R^2$, aliphatic group independently, has from 1 to about 16 carbon atoms, desirably from 2 to about 8 carbon atoms, and preferably from about 2 to about 5 carbon atoms; with the proviso that at least one $R^1$ or $R^2$ is not hydrogen, and wherein $R^3$ is either H or $CH_3$. In a preferred embodiment, the acrylamide polymer is poly(N-isopropyl-acrylamide) (PNIPAM), wherein $R^1$ or $R^3$ are hydrogen and $R^2$ is an isopropyl group. Additional examples for either or both of $R^1$ or $R^2$ are propyl; butyl; isobutyl; t-butyl; 2-methylpropyl; pentyl; isopentyl; amyl; 1,1-dimethylpropyl; 1,2-dimethylpropyl; or 2,2-dimethylpropyl. In other embodiments, $R^1$ or $R^2$ can be the same and can be for example, diethyl, dipropyl, dibutyl, or dipentyl.

Comonomers which can optionally be present along with the acrylamide monomer in an acrylamide copolymer of the present invention include one or more of (meth)acrylic acid, (meth)acrylates having from 1 to about 16 carbon atoms in the acid derived portion of the monomer, ionic comonomers such as poly(N-isopropylacrylamide-co-acrylic acid), and nanoparticles such as conductive nano-Pt or nano-Au metallic particles or nanodielectric particles such as polystyrene. The nanoparticles can be incorporated into an acrylamide polymer or copolymer by polymerizing the desired nanoparticles onto the polymer via a functional group containing side chain. For example, the side chain of the polymer can be activated acid, while the nanoparticles are modified with amine groups. The attachment of the nanoparticles can be achieved through amide formation.

The poly(N-substituted)(meth)acrylamide (co)polymer is substantially linear, and is preferably free of crosslinking in one embodiment. The term (co)polymer means that the composition can be either a polymer, i.e. homopolymer, or a copolymer of two or more different monomers. It is to be understood that the linear (co)polymer can have pendant side chains, and the (co)polymer is linear in the sense that the same is substantially free of crosslinking, and preferably free of crosslinking. The weight average molecular weight of the linear poly(N-substituted)(meth)acrylamide (co)polymer is greater than $1.0 \times 10^5$ g/mol or greater than about $2.1 \times 10^7$ g/mol, desirably from about $5.0 \times 10^5$ g/mol or about $2.1 \times 10^7$ g/mol to about $5.0 \times 10^8$ g/mol, and preferably from about $5.0 \times 10^5$ g/mol to about $4.5 \times 10^7$ g/mol. If the molecular weight of the linear poly(N-substituted)(meth)acrylamide copolymer is too low, it is relatively hard to precipitate out of solution in response to radiation pressure. Poly(N-substituted)(meth)acrylamide copolymers having a higher molecular weight are desired, but are relatively hard to make. Methods for synthesizing poly(N-substituted)(meth)acrylamide (co)polymers are known in the art, see Macromolecules 2004, 37 1031-1036, for example. The poly(N-substituted)(meth)acrylamide (co)polymers can be crosslinked, with the proviso that the (co)polymers utilized are homogeneous in solution and the composition is transparent or substantially optically clear or optically clear below the threshold radiation pressure. Accordingly, such crosslinked poly(N-substituted)(meth)acrylamide (co)polymers are distinguished from prior art crosslinked poly-N-isopropylacrylamide polymers and compositions disclosed in U.S. Pat. Nos. 6,097,530, 6,165,389 and 6,014,246 wherein crosslinked PNIPAM in the form of spherical particles are utilized. The weight average molecular weight of the crosslinked poly(N-substituted)(meth)acrylamide (co)polymer is generally greater than or equal to the molecular weight values set forth for the substantially linear (co)polymer described above.

The solution in which the phase changing (co)polymer is contained depends on the ability of the solution to solubilize the polymer. Environmentally friendly solutions or solvents are preferred, especially when the composition is utilized in an optical device adapted to be utilized in close contact with the eye(s) of a person, such as glasses, goggles, telescopes, binoculars, or the like. Suitable solutions or solvents include water and deuterated water, with water being preferred. For laser light or radiation whose wavelength is close to the absorption of water or deuterated water, respectively, the use of respective solvent is beneficial since it will heat the solvent, facilitating the precipitation of the polymer.

The phase changing (co)polymer is present in the solution in an effective amount to exhibit a desired response, i.e. light scattering, upon exposure to light above a threshold intensity or radiation pressure. The (co)polymer concentration in the solution is generally greater than about 0.1 mg/mL, and desirably ranges from about 0.1 or about 0.2 mg/mL to about 50 mg/mL, and preferably from about 8 mg/mL to about 20 mg/mL of solution. That said, the concentration of the (co)polymer in the solution can vary depending on the molecular weight of the polymer. If the concentration of the phase changing (co)polymer is too low, there may not be enough (co)polymer material in the path of the incident beam or ray to scatter light, and if concentration is too high, response time may be slower than desired due to the relatively high viscosity of the solution. For example, when linear PNIPAM having a molecular weight of $3.95 \times 10^7$ g/mol is utilized as the phase changing polymer in a solution of water, the concentration is preferably about 10 mg/mL.

The solution, in addition to containing the phase changing (co)polymer, can include other components that do not substantially decrease the light scattering capability of the (co) polymer. For example, various salts can be added to aid in precipitation including, but not limited to, sodium salts such as sodium chloride and sodium fluoride; calcium salts such as calcium chloride, and calcium sulfate; and potassium salts such as potassium chloride. Halogen salts such as potassium fluoride can be utilized, as well as Hofmeister series salts. It is desirable that any additives added to the compositions of the present invention maintain or substantially maintain the optical clarity of the composition. The amounts of additives are generally dependent on the particular additive chosen. Thus, the amount of additive or salt can vary. The concentration of salt can be increased to reduce the threshold of the polymer against radiation pressure. The concentration of the salt should be maintained as high as possible without inducing spontaneous precipitation of the polymer under working environment, i.e. under ambient temperature without laser light. For example, 0.8 M of potassium fluoride will induce precipitation of linear PNIPAM at ~23° C.

It is desirable to maintain the temperature of the composition including the carrier or solvent solution and (co)polymer below the lower critical solution temperature of the (co)polymer utilized prior to exposure to light having an intensity or radiation pressure above a threshold level so that the (co) polymer is soluble and the composition is substantially optically clear. Of course, it is desirable to maintain a temperature as close to the lower critical solution temperature as possible in order to aid in precipitation when the threshold radiation pressure is exceeded. For example, the linear PNIPAM has a lower critical solution temperature of about 32° C., above which the polymer folds and precipitates from solution.

As the compositions of the present invention are generally liquids, it is desirable to maintain the compositions in a container, which is preferably optically clear. The term "optically clear" means that the object at issue does not absorb substantially any light, and therefore transmits substantially all or all light incident thereon. Suitable containers include, but are not limited to, glass, quartz, optically or substantially optically clear polymers such as polycarbonate, and the like. The container utilized should be non-reactive with the composition. The container may be either open to the atmosphere or sealed, with a sealed container preferred in order to prevent evaporation of the solution therein which can change the concentration of the (co)polymer.

When the radiation pressure of light or radiation such as from a laser is low, the composition of the present invention is clear or substantially clear below the (co)polymer lower critical solution temperature and the intensity of the light is not affected, and all or substantially all of the light passes through the solution composition. When the radiation pressure is above a threshold value, however, the polymer in the composition solution precipitates and reduces radiation pressure by scattering. The precipitated particles substantially immediately disappear, i.e. solubilize, when the radiation pressure is reduced below the threshold value. Both on-off responses, namely, precipitation and solubilizing occur within microseconds, such as within an upper limit of about 200 microseconds. Threshold radiation pressure depends on a number of factors including the polymer utilized. It is desirable to have a threshold radiation pressure value of about 1 W/cm$^2$ at room temperature i.e. an ambient temperature from about 20° C. (68° F.) to about 25° C. (77° F.). That said, the composition is desirably utilized to produce a threshold radiation pressure value that can range from about 1 W/cm$^2$ to about $1.0 \times 10^9$ W/cm$^2$ at room temperature. The upper limit is an estimation based on 10 W laser focused at an area of 1 µm$^2$. For example, a container containing ($3.95 \times 10^7$ g/mol) linear PNIPAM in deuterium at concentration of 10 mg/mL has a threshold value of 2,000 W/cm$^2$ at room temperature, which is sufficient to protect typical optical components.

Figure 2:
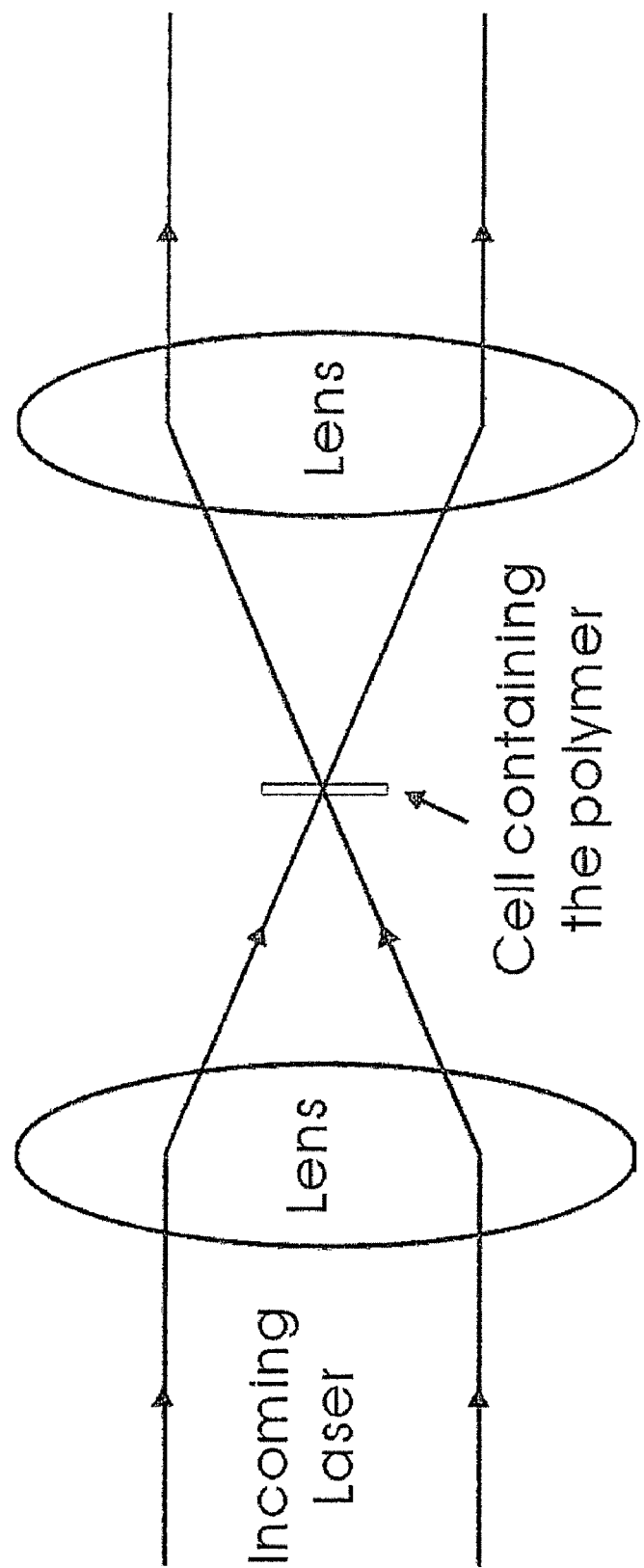
FIG. 2 schematically illustrates a simple optical device that can protect optical components from high radiation pressure laser beams.

An example of an optical device is shown in FIG. 2, wherein a container containing a composition of the present invention including linear PNIPAM ($3.95 \times 10^7$ g/mol) at a concentration of 10 mg/mL in water is placed at the focal point between two lenses constituting a simple telescope. Such telescopes are routinely utilized in optical designs that change the spot size of an incoming laser, collimate laser beams and provide magnification to observe small objects. Many companies produce telescopes that are flexible in beam size magnification by adjusting the positions of the lenses. By placing the container on a translational stage, the setup can be readily incorporated into such telescopes. The advantage of this design is that it allows a normal optical alignment under certain laser intensities, i.e. below the threshold radiation pressure, while preventing the alignment or blocking the passage of the laser beam when the radiation pressure is higher than the threshold. Accordingly, the compositions of the present invention can limit the power of radiation in order to protect sensitive downstream optical components, such as, but not limited to, polarized beam splitters, various wave plates and optical coatings that can be easily damaged by light, such as from a laser with a high power intensity.

Particularly in the field of eye protection, there are several unique properties exhibited by the compositions of the present invention. First, the response of the composition is highly localized. The precipitation only occurs inside the area where the incident light beam contacts the composition. This suggests the imaging field outside the beam pathway is not affected, which is important for people in a potentially dangerous situation where a continuous and unobstructive observation of surroundings is critical for survival. Second, low radiation pressure light is not affected by the compositions of the present invention. This ensures a high quality visual evaluation of the environment when the composition is subjected to a radiation pressure of light below the threshold value. Furthermore, the response of the composition is independent of light wavelength. The compositions of the present invention are superior to existing products where protection is limited to certain light wavelengths.

The reversible responses to radiation pressure empower the phase changing (co)polymer material to sense and react to relatively high intensity light, such as from a laser beam. The high radiation pressure light generates a gradient force, wherein the (co)polymer sensitive to radiation pressure shrinks and precipitates under high force gradient and swells and dissolves when the gradient is low. Radiation pressure is proportional to trapping force, $F_{grad}=(|\alpha|/2)\nabla[E^2]$, here $\nabla[E^2]$ is related to the gradient of an electric field in a laser beam.

The use of lasers in the battlefield has rapidly become a reality. The lasers have already been deployed to detonate explosive devices and destroy optical reconnaissance instruments. If used against battlefield personnel, lasers can generate irreversible vision injuries. It is, therefore, imperative to engineer protective schemes that efficiently prevent damage from high intensity, high radiation pressure emitting lasers while maintaining a non-obstructive passage for visible light at low power. Various schemes exist for laser protections. Almost all of existing products adopt a passive mechanism where light absorbing materials attenuate laser beams indistinguishably over a spectrum of intensities across full imaging field. Although intensity-selective organic materials exist, they suffer from a narrow wavelength spectrum. For example, optical limiters made of $C_{60}$ fullerene can pass 532 nm at low intensity while attenuating it at a high power. Although significant progress has been achieved in the past few years, materials are still to be sought to assuage the damaging laser at broadband wavelength without interfering with the light at low intensity or limiting the field of view. The present invention material that responds locally against high radiation pressure will be a welcome addition to the arsenal of laser protection weaponry. Such material can either be used directly against the incoming laser beam, and/or as a sensor/actuator to trigger one or more subsequent protection schemes after the material responses to a high radiation pressure laser.

The compositions of the present invention can be utilized in substantially any optical device wherever desired. Non-limiting examples of optical devices include goggles, telescopes, binoculars, and flexible optical coatings. The compositions of the present invention provide optical devices useful as optical switches, optical limiters, and/or optical filters that are responsive to changes in radiation pressure. An optical switch generally refers to an optical device that defracts light at one radiation pressure and transmits light at a second radiation pressure below a threshold level. Such a device is, therefore, switched on or off by changing light radiation pressure. An optical filter is generally an optical device that allows substantially all light but that of a given radiation pressure greater than a threshold value to pass therethrough. An optical limiter generally refers to an optical device that allows transmission of a laser beam whose radiation pressure is below a certain threshold; whereas the light is blocked when the radiation pressure is higher than the threshold. A flexible optical coating refers to a flexible protective coating that allows the passage of a laser beam only when its radiation pressure is below a certain threshold.

EXAMPLES

A container having an interior width of 180 μm in the direction parallel to a light beam adapted to be passed through the container and walls having a thickness of 280 μm was filled with a composition comprising linear PNIPAM polymer having a molecular weight of $3.95 \times 10^7$ g/mol weight average at a concentration of 10 mg/mL in $D_2O$. A laser having a wavelength of 1064 nanometers and a power of 224 mW was turned on and a beam of light therefrom was directed through the container and the composition therein. The radiation pressure of the laser was about $285 \times 10^5$ W/cm$^2$. As illustrated in FIG. 1A, the focus of the laser light passing through the container and composition was imaged by a CCD camera equipped with a neutral density filter. It was determined that no PNIPAM precipitated particles were formed at time zero. A second experiment was also conducted utilizing a laser having a wavelength of 532 nanometers and a power of 25 mW, which gave a radiation pressure of $32 \times 10^5$ W/cm$^2$. Similar results were obtained.

FIG. 1B illustrates the scattering effect of the composition 240 ms after the 224 mW 1064 nm laser was turned on. Due to the scattering of the particles that have already appeared at the laser focus and its surrounding area, the radiation pressure of the light was reduced.

FIG. 1C illustrates the image from the CCD camera formed wherein the light from the 224 mW laser was defocused after 240 ms of contact with the composition in the container. Notice the much increased light scattering and much reduced radiation pressure and laser intensity. The experiments were performed utilizing a laser tweezers instrument and the images have a 100 micrometer range.

While in accordance with the patent statutes the best mode and preferred embodiment have been set forth, the scope of the invention is not limited thereto, but rather by the scope of the attached claims.

What is claimed is:

1. A radiation pressure activatable light filtering device, comprising:
   a container having a substantially optically clear portion through which light can pass; and
   a composition disposed in the container comprising a linear poly(N-substituted)(meth)acrylamide (co)polymer free of crosslinking and having a weight average molecular weight greater than $2.1 \times 10^7$ g/mol in a solution, wherein the composition is substantially optically clear below a lower critical solution temperature of the composition, wherein the (co)polymer is capable of undergoing a reversible phase transition that forms microdomains having a different refractive index in the solution in response to being exposed to light having a radiation pressure above a threshold value thereby causing the light above the threshold value incident on the phase transformed (co)polymer to scatter, and wherein the (co)polymer is soluble in the solution below the lower critical solution temperature and prior to exposure to said light above the threshold value.

2. The device according to claim 1, wherein the (co)polymer includes at least one repeat unit of the formula:

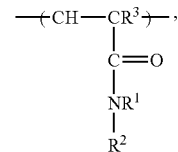

wherein each $R^1$ and $R^2$, independently, is hydrogen, a linear or branched aliphatic group having from 1 to about 16 carbon atoms, an aromatic group, and aryl-aliphatic group, a cyclic group, a heterocyclic group including the nitrogen atom, or one of said groups chemically modified with a non-carbon atom with the proviso that at least one of $R^1$ and $R^2$ is not hydrogen, and wherein $R^3$ is either hydrogen or $CH_3$.

3. The device according to claim 2, wherein the (co)polymer is poly(N-isopropylacrylamide).

4. The device according to claim 2, wherein the (co)polymer has a weight average molecular weight of greater than $2.1 \times 10^7$ g/mol to about $5.0 \times 10^8$ g/mol, and wherein the (co)polymer is present in an amount from about 0.1 mg/mL to about 50 mg/mL of solution.

5. The device according to claim 4, wherein the device is an optical limiter, an optical switch, or optical coating.

6. The device according to claim 2, wherein the solution is water or deuterated water, and wherein the weight average molecular weight of the linear (co)polymer is $3.0 \times 10^7$ to about $5.0 \times 10^8$ g/mol.

7. The device according to claim 6, wherein the (co)polymer is present in an amount from about 0.2 mg/mL to about 20 mg/mL of solution, wherein the (co)polymer is poly(N-isopropylacrylamide), and wherein the threshold value is greater than or equal to 2000 W/cm$^2$.

8. The device according to claim 1, wherein the threshold value is from about 1 to about $1.0 \times 10^9$ W/cm$^2$, wherein the response is independent of radiation wavelength, and wherein a response time of the phase transition is less than 200 microseconds.

9. The device according to claim 1, wherein a comonomer is present and comprises (meth)acrylic acid, a (meth)acrylate having from 1 to about 16 carbon atoms in the acid derived portion of the monomer, an ionic comonomer, or a nanoparticle, or a combination thereof.

10. The device according to claim 1, wherein the composition further includes a salt.

11. The device according to claim 10, wherein the salt is a sodium salt, a calcium salt, a potassium salt, a halogen salt or a Hofmeister series salt or a combination thereof.

12. The device according to claim 1, wherein the device further comprises a first lens and a second lens, with a container disposed between the first lens and the second lens.

13. The device according to claim 1, wherein the optical device comprises glasses, goggles, a telescope, a binocular, or a flexible optical coating, or a combination thereof.

* * * * *